(12) United States Patent
Cho et al.

(10) Patent No.: US 9,615,939 B2
(45) Date of Patent: Apr. 11, 2017

(54) SPINAL FUSION SURGERY INSTRUMENT FOR IMPLANTING AND INTERVERTEBRAL CAGE THEREOF

(71) Applicant: INTAI Technology Corporation, Taichung (TW)

(72) Inventors: Ming-Cheng Cho, Changhua (TW); Dian-Ying Lin, Changhua County (TW); Yung-Fang Tsai, Taichung (TW); Shin-Chang Chuang, Taichung (TW)

(73) Assignee: INTAI TECHNOLOGY CORPORATION, Taichung (TW)

( * ) Notice: Subject to any disclaimer, the term of this patent is extended or adjusted under 35 U.S.C. 154(b) by 11 days.

(21) Appl. No.: 14/828,266

(22) Filed: Aug. 17, 2015

(65) Prior Publication Data
US 2016/0317323 A1    Nov. 3, 2016

(30) Foreign Application Priority Data
Apr. 28, 2015 (TW) .............................. 104113539 A

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/4455* (2013.01); *A61F 2/4657* (2013.01); *A61F 2002/30112* (2013.01); *A61F 2002/30471* (2013.01); *A61F 2002/30538* (2013.01); *A61F 2002/30784* (2013.01); *A61F 2002/4627* (2013.01); *A61F 2002/4662* (2013.01)

(58) Field of Classification Search
CPC ...................................................... A61F 2/4611
See application file for complete search history.

(56) References Cited

U.S. PATENT DOCUMENTS 7,575,580 B2 * 8/2009 Lim ...................... A61F 2/4465 606/246
7,976,549 B2 * 7/2011 Dye ...................... A61F 2/4465 606/86 A (Continued)

FOREIGN PATENT DOCUMENTS

TW          I441615 B      6/2014
TW          I 465229 B     12/2014

*Primary Examiner* — Jan Christopher Merene
(74) *Attorney, Agent, or Firm* — Muncy, Geissler, Olds & Lowe, P.C.

(57) ABSTRACT

A spinal fusion surgery instrument for implanting and an intervertebral cage thereof are provided. The spinal fusion surgery instrument includes a body, a gripper subassembly, a first control subassembly, and a second control subassembly. The first control subassembly is provided to generate a displacement between a first connecting member and a second connecting member of the gripper subassembly to change the angle of gripper of the intervertebral cage. The second control subassembly is provided to enable a first gripper member and a second gripper member of the gripper subassembly separating smoothly from the dowel pins of the intervertebral cage. By means of the operation model, the spinal fusion surgery instrument may be controlled easily, and the orientation of the intervertebral cage may be promoted in the process of the surgery.

10 Claims, 6 Drawing Sheets

(56) References Cited

U.S. PATENT DOCUMENTS

| | | | |
|---|---|---|---|
| 7,988,695 B2 * | 8/2011 | Dye | A61F 2/4611 |
| | | | 606/86 A |
| 8,012,156 B2 | 9/2011 | Marquez Alvarez | |
| 8,114,092 B2 | 2/2012 | Altarac et al. | |
| 8,608,746 B2 | 12/2013 | Kolb et al. | |
| 8,696,681 B2 | 4/2014 | Harris et al. | |
| 8,858,637 B2 * | 10/2014 | Milz | A61F 2/4465 |
| | | | 623/17.16 |
| 2006/0229627 A1 * | 10/2006 | Hunt | A61B 17/1659 |
| | | | 606/86 R |
| 2006/0235426 A1 * | 10/2006 | Lim | A61F 2/4465 |
| | | | 606/99 |
| 2010/0137922 A1 | 6/2010 | Hunt et al. | |
| 2012/0209383 A1 * | 8/2012 | Tsuang | A61F 2/4603 |
| | | | 623/17.12 |

* cited by examiner

SPINAL FUSION SURGERY INSTRUMENT FOR IMPLANTING AND INTERVERTEBRAL CAGE THEREOF

CROSS-REFERENCE TO RELATED APPLICATION

This application claims the benefit of Taiwan Patent Application No. 104113539, filed on Apr. 28, 2015, in the Taiwan Intellectual Property Office, the disclosure of which is incorporated herein in its entirety by reference.

BACKGROUND OF THE INVENTION

1. Field of the Invention

The present invention generally relates to an implant instrument and an intervertebral cage thereof, in particular to the implant instrument and the intervertebral cage thereof which are feasible to be applied to the transforaminal lumbar interbody fusion (TLIF).

2. Description of the Related Art

Generally, the vertebrae disease is caused by long-term inappropriate pose, sport injury or comes with ages. When the intervertebral disk is damaged severely, two adjacent spine bones may approach with each other abnormally to suppress the surrounding nerves and the pain caused by the nerve compression may disable the patient from exercising.

Currently, the most common treatment is to implant an intervertebral cage into a location between two adjacent spine bones by means of an implant instrument, so as to increase or recover the distance between the two adjacent spine bones and avoid the nerves from being suppressed. In the case of the treatment, the clinical surgeon operates the discectomy and then implants the intervertebral cage into a location between two adjacent spine bones to recover the stability of the vertebrae. The TLIF generally has three manners of anterior, posterior and transforaminal lumbar, and the used intervertebral cage may vary with the manners. In practice, the transforaminal lumbar has advantages of less negative effect upon the surrounding tissues of the patient and shorter postoperative healing time, compared with the other surgery. However, as far as the surgeon is concerned, the transforaminal lumbar has a smaller operative field and a higher demand in terms of operating the surgical instruments. When the implant instrument and the intervertebral cage are implanted into the human body, the surgeon can only operate the surgical instruments according to the instinct, touch and experience as it is difficult to do through visual contact. In addition, when the surgeon plans to separate the implant instrument from the intervertebral cage, even the intervertebral cage is placed in the accurate position, the intervertebral cage is easy to deviate from its accurate position due to the motion of the implant instrument, such that the repositioning is necessary and the surgery time has to be extended.

As a result, the inventor of the present invention provides a spinal fusion surgery instrument for implanting and an intervertebral cage thereof which aim to improve the shortcomings of the current technique, so as to promote the clinical or medical practicability.

SUMMARY OF THE INVENTION

In view of the aforementioned problem, a primary objective of the present invention provides a spinal fusion surgery instrument for implanting and an intervertebral cage thereof which change an angle with respect to the location of the intervertebral cage by adjusting the relative position between each member of the gripper subassembly, so that the complicated operation of the implant instrument is simplified to reduce the arrangement time of the intervertebral cage.

In view of the aforementioned problem, a primary objective of the present invention provides a spinal fusion surgery instrument for implanting to reduce the expected factors such as elastic fatigue, delayed movement and so on of the elastic member or the flexible member by adjusting the relative movement between the stiffener members, such that the uncertainty in the operational process can be avoided. In addition, the first fastening slot and the second fastening slot of the jaw portion can separate from the gripping end of the intervertebral cage by enabling the stop pin resists against the guiding shapes of the first gripping member and the second gripping member, such that the technical problems such as vibration, displacement and so on can be resolved when the implant instrument releases the intervertebral cage.

In view of the aforementioned problem, a primary objective of the present invention provides an intervertebral cage of a spinal fusion surgery, wherein the guiding end of the body thereof is a streamline shape with a sharp angle, which is able to peel off or penetrate the surrounding tissues of the intervertebral disks effortlessly and effectively reduce the residual force formed between the intervertebral disks. The dowel pins disposed in parallel are able to be gripped by the gripper subassembly of the implant instrument, and also applied in the positioning by the C-arm during the process of the surgery, such that the implanted direction and angle of the intervertebral cage of the present invention can be adjusted immediately by the relative position of the dowel pins and the auxiliary dowel pin, so as to shorten the positioning time.

The present invention provides an implant instrument for gripping and implanting an intervertebral cage into a location between two adjacent spine bones. The intervertebral cage may include a gripping end and a guiding end. The implant instrument may include a body, a gripper subassembly, a first control subassembly, and a second control subassembly. The body may include a grasp rod and a fixed rod. The fixed rod has a first end and a second end, wherein the first end is disposed at the grasp rod, the second end has a shape corresponding to the gripping end of the intervertebral cage. The fixed rod may be disposed with a first guiding slot and a second guiding slot which communicate with the second end. The fixed rod may have a thread outer diameter near a side of the first end and may further include a straight limit slot near a side of the second end.

The gripper subassembly may include a first connecting member, a first gripping member, a second connecting member and a second gripping member. The first connecting member is connected to the first gripping member and disposed in the first guiding slot, the second connecting member is connected to the second gripping member and disposed in the second guiding slot. The first connecting member has a first thread structure, the second connecting member has a second thread structure, the first gripping member has a first fastening slot, and the second gripping member has a second fastening slot, wherein the first fastening slot and the second fastening slot may form a jaw portion to grip the gripping end of the intervertebral cage. The first control subassembly may include a first rotating shaft and a second rotating shaft, the first rotating shaft may be connected to the second rotating shaft and sleeved outside the fixed rod, an internal thread of the first rotating shaft is screwed to the first thread structure, and an internal thread of the second rotating shaft is screwed to the second thread structure. The second control subassembly may include a sleeve and a gripping rotating shaft, the sleeve is connected to the gripping rotating shaft and sheathed outside the fixed rod. The sleeve may further have a stop pin inserted into the limit slot, and an internal thread of the gripping rotating shaft is screwed to a thread outer diameter of the fixed rod.

When rotating the first control subassembly, the first connecting member and the second connecting member may respectively be moved to opposite directions along the first guiding slot and the second guiding slot to change a relative position between the jaw portion and the intervertebral cage so as to change an angle with respect to the location of the intervertebral cage. When the second control subassembly is rotated to move the sleeve toward the first end of the fixed rod, the stop pin resists against the first gripping member and the second gripping member for enabling the jaw portion open to release the intervertebral cage; otherwise, when the second control subassembly is rotated to move the sleeve toward the second end of the fixed rod, the jaw portion may be closed.

Preferably, the first guiding slot and/or the second guiding slot may further include a limit slot near the side of the first end of the fixed rod for limiting the operation of the gripper subassembly.

Preferably, the implant instrument of the present invention may further include a measuring unit for measuring a depth where the implant instrument inserts into vertebra. The measuring unit is sheathed outside the sleeve.

Preferably, the first thread structure, the second thread structure, the thread outer diameter or a combination thereof may be a single thread or a multiple thread.

Preferably, the fixed rod, the first connecting member, the second connecting member or a combination thereof may be integral or assembly-type.

According to the foregoing objective, the present invention further provides an intervertebral cage being gripped and implanted into a location between two adjacent spine bones by an implant instrument. The intervertebral cage includes a body, dowel pins and at least one auxiliary dowel pin. The body may be a structure including a plurality of penetration cavities which are mutual interlaced. The body may have a guiding end and a gripping end. The gripping end may have two dowel holes in parallel, and the gripping end may be disposed with at least one auxiliary dowel hole.

Two dowel pins may be respectively inserted into the two dowel holes, and at least one auxiliary dowel pin may be inserted into the corresponding auxiliary dowel hole. The two dowel pins and the at least one auxiliary dowel pin may assist in displaying and guiding a dynamic relative location of the body in the process of the surgery, such that the positioning accuracy of the surgery can be promoted.

Preferably, the intervertebral cage may be shaped with a guided circumferential angle to avoid damaging surrounding tissues accidently in the process of the surgery.

Preferably, the plurality of penetration cavities may remove a volume of the body by 30-70%.

BRIEF DESCRIPTION OF THE DRAWINGS

The detailed structure, operating principle and effects of the present invention will now be described in more details hereinafter with reference to the accompanying drawings that show various embodiments of the disclosure as follows.

DETAILED DESCRIPTION OF THE PREFERRED EMBODIMENTS

Hereinafter, embodiments of the present invention will be described in detail with reference to the accompanying drawings so that those skilled in the art to which the present invention pertains can realize the present invention. As those skilled in the art would realize, the described embodiments may be modified in various different ways, all without departing from the spirit or scope of the present invention.

The exemplary embodiments of the present invention will be understood more fully from the detailed description given below and from the accompanying drawings of various embodiments of the disclosure, which, however, should not be taken to limit the disclosure to the specific embodiments, but are for explanation and understanding only.

Figure 1:
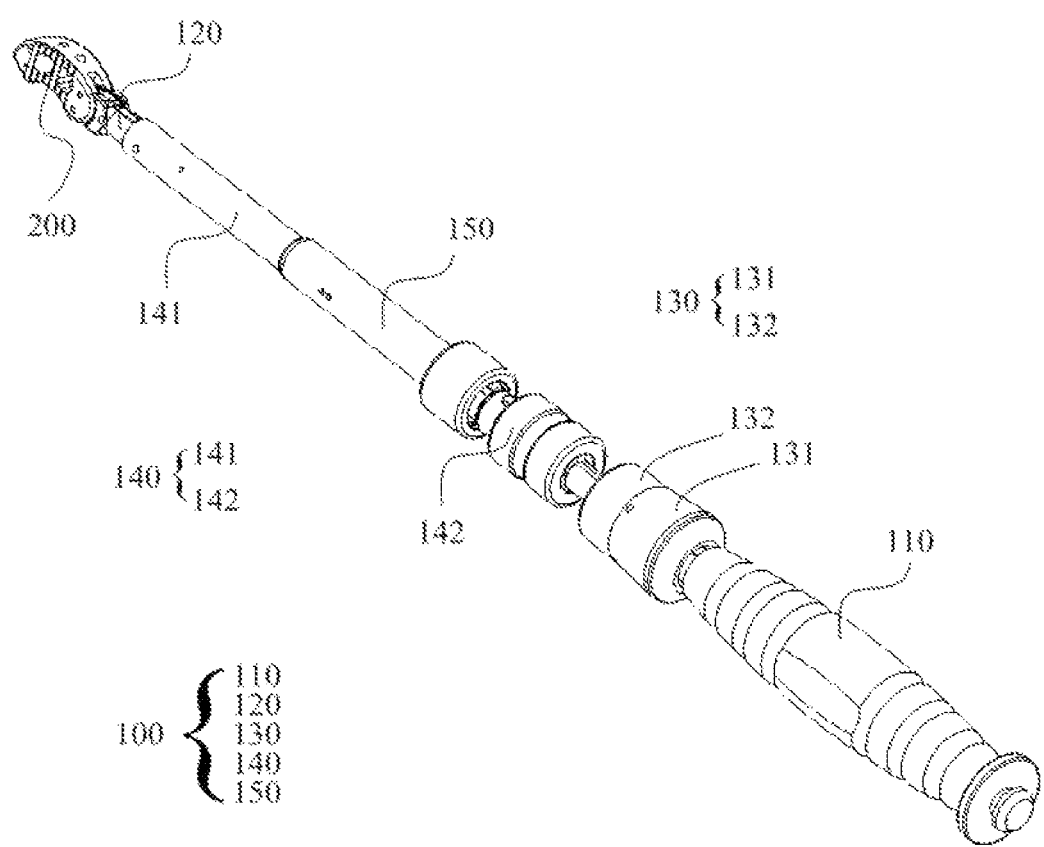
FIG. 1 is a schematic diagram of the spinal fusion surgery instrument for implanting and the intervertebral cage thereof of the present invention.
Figure 2:
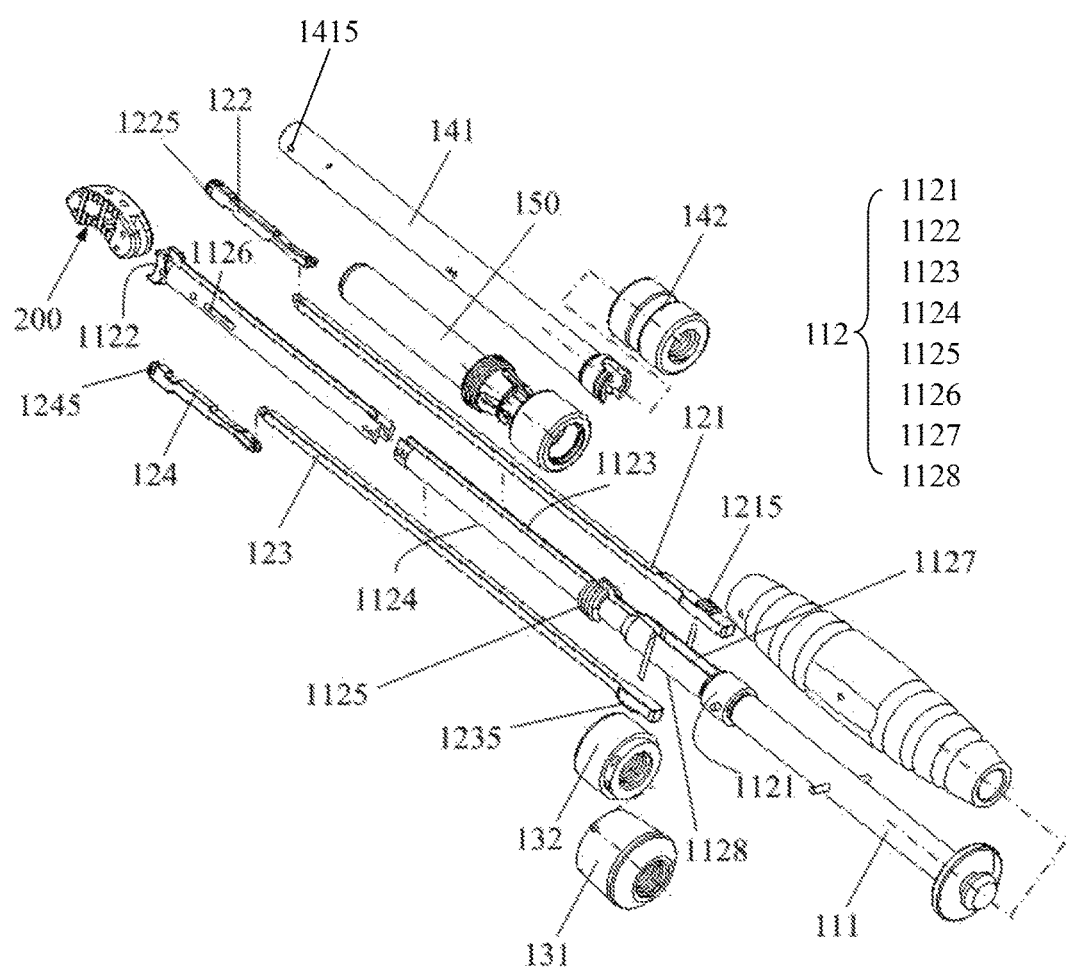
FIG. 2 is an explosion diagram for showing the spinal fusion surgery instrument for implanting of the present invention.
Figure 3:
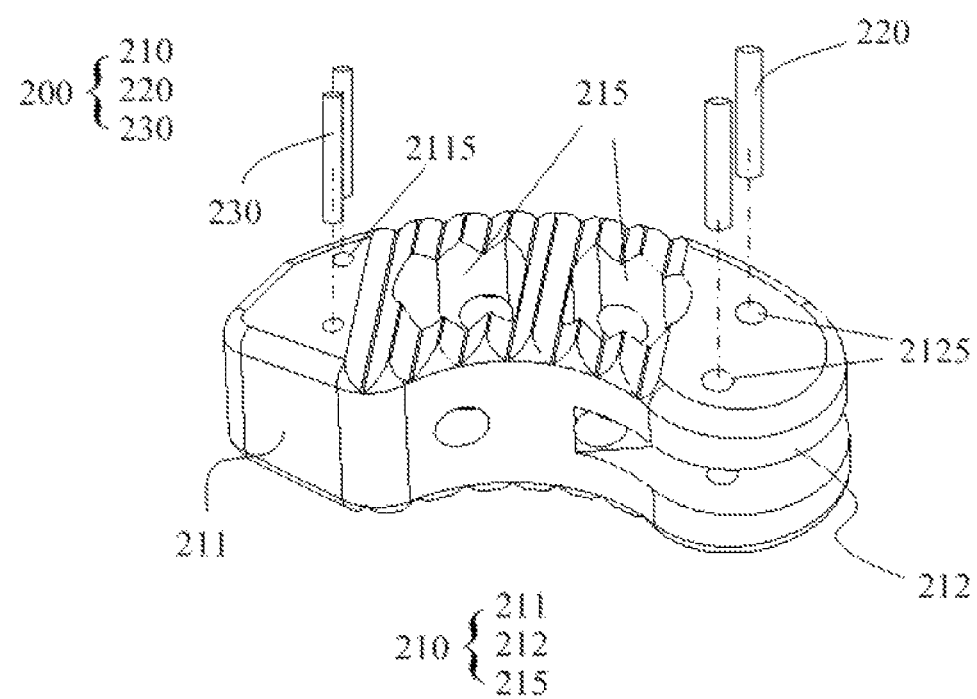
FIG. 3 is a schematic diagram of the intervertebral cage of the present invention.

Please refer to FIG. 1, FIG. 2, and FIG. 3. As shown in the FIGS., an implant instrument 100, which may be a spinal fusion surgery instrument for implanting, of the present invention is applied to grip and implant an intervertebral cage 200 to a location between two adjacent spine bones. The intervertebral cage 200 has a guiding end 211 and a gripping end 212. The implant instrument 100 includes a body 100, a gripper subassembly 120, a first control subassembly 130, a second control subassembly 140 and a measuring unit 150. The measuring unit 150 is sheathed outside the sleeve 141 of the second control subassembly 140. The body 110 includes a grasp rod 111 and a fixed rod 112. The gripper subassembly 120 includes a first connecting member 121, a first gripping member 122, a second connecting member 123 and a second gripping member 124. The first control subassembly 130 includes a first rotating shaft 131 and a second rotating shaft 132. The second control subassembly 140 includes the sleeve 141 and a gripping rotating shaft 142. The fixed rod 112 has a first end 1121 and a second end 1122. The first end 1121 may be assembled on the grasp rod 111 by means of screwing, sleeving, and so on. The second end 1122 has a shape corresponding to the gripping end 212. The fixed rod 112 has a thread outer diameter 1125 near a side of the first end 1121.

More precisely, a length of the fixed rod 112 is designed according to the necessary operative field and the operating space based on the injured area. When the required length of the fixed rod 112 is short, the fixed rod 112 may be formed integrally. The fixed rod 112 with the shorter length has a better precise operation, but the operative field may be shielded by the surgical instruments. For the sake of achieving a better operative field the fixed rod 112 is designed with a longer length as such with an assembly-type fixed rod 112 may be operated. The diagrams of the present invention apply an assembly-type fixed rod 112 as an exemplary embodiment. In addition to the better operative field, the assembly-type fixed rod 112 is easy to be treated and assembled. The dual structure of the fixed rod 112 may be assembled from the two sides of the sleeve 141 respectively, and then a pin is used to fix the dual structure of the fixed rod 112 as integrity. In practice, the first connecting member 121 and the second connecting member 123 may be integral or assembly-type according to the actual requirements.

The fixed rod 112 is disposed with a first guiding slot 1123 and a second guiding slot 1244 which communicate with the second end 1122. In practice, the first guiding slot 1123 and the second guiding slot 1124 are respectively disposed at an upper side and a lower side of the fixed rod 112 in parallel, so that the fixed rod 112 is shaped as a H-shaped longer shaft as a whole. Moreover, the first guiding slot 1123 and the second guiding slot 1124 respectively include limit slots 1127, 1128 near the first end 1121. The first connecting member 121 is connected to the first gripping member 122 and disposed in the first guiding slot 1123 to move linearly along the first guiding slot 1123. Similarly, the second connecting member 123 is connected to the second gripping member 124 and disposed in the second guiding slot 1124 to move linearly along the second guiding slot 1124. In practice, the lengths of the limit slots 1127, 1128 may be applied to respectively limit the range of motion of the first connecting member 121 and the second connecting member 123.

Figure 4:
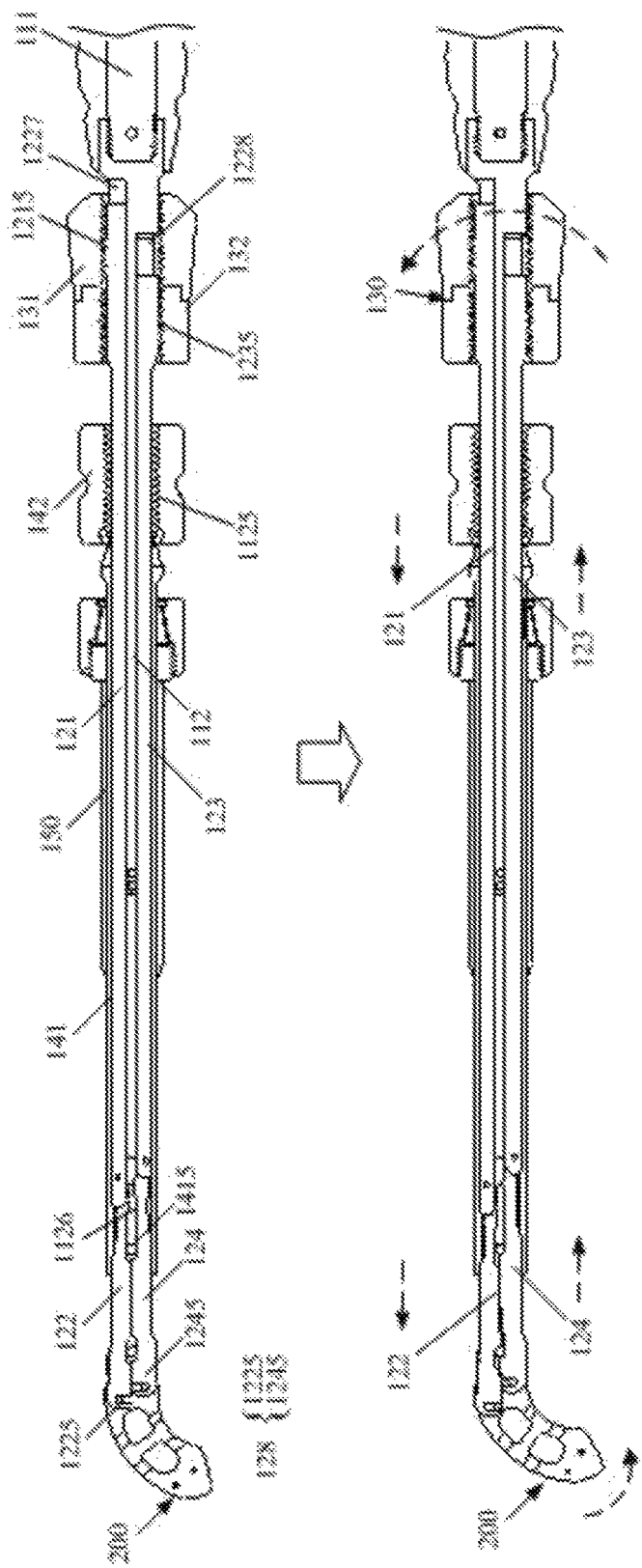
FIG. 4 is a schematic diagram for showing the placement operations of the intervertebral cage of the present invention.

Please refer to FIG. 1 and FIG. 4 together. As shown in the FIGS., the first rotating shaft 131 of the first control subassembly 130 is connected to the second rotating shaft 132 to rotate simultaneously. The first control subassembly 130 is sleeved outside the fixed rod 112 for being used by a surgeon. An internal thread of the first rotating shaft 131 is screwed to the first thread structure 1215 disposed at one end of the first connecting member 121, and an internal thread of the second rotating shaft 132 is also screwed to a second thread structure 1235 of the second connecting member 123. When the surgeon rotates the first control subassembly 130, the first connecting member 121 and the second connecting member 123 respectively are moved to opposite directions along the first guiding slot 1123 and the second guiding slot 1124 of the fixed rod 112. In practice, the first thread structure 1215, the second thread structure 1235, the thread outer diameter 1125 of the fixed rod 112 or a combination thereof may be a single thread characterized of accurate motion or a multiple thread which is applied to increase the operating space and shorten the rotation time.

To be precise, the first gripping member 122 of the gripper subassembly 120 has a first fastening slot 1225, and the second gripping member 124 of the gripper subassembly 120 has a second fastening slot 1245. The first fastening slot 1225 and the second fastening slot 1245 are applied to form a jaw portion 128 to grip the gripping end 212 of the intervertebral cage 200. In practice, the first fastening slot 1225 and the second fastening slot 1245 are disposed in parallel to grip a dowel pin 220 of the intervertebral cage 200. For example, when rotating the first control subassembly 130, the first connecting member 121 may move to the second end 1122 along the first guiding slot 1123 and the second connecting member 123 may move to the first end 1121 along the second guiding slot 1124. The dislocation generated between the first connecting member 121 and the second connecting member 123 changes an angle with respect to the location of the intervertebral cage 200.

Figure 5:
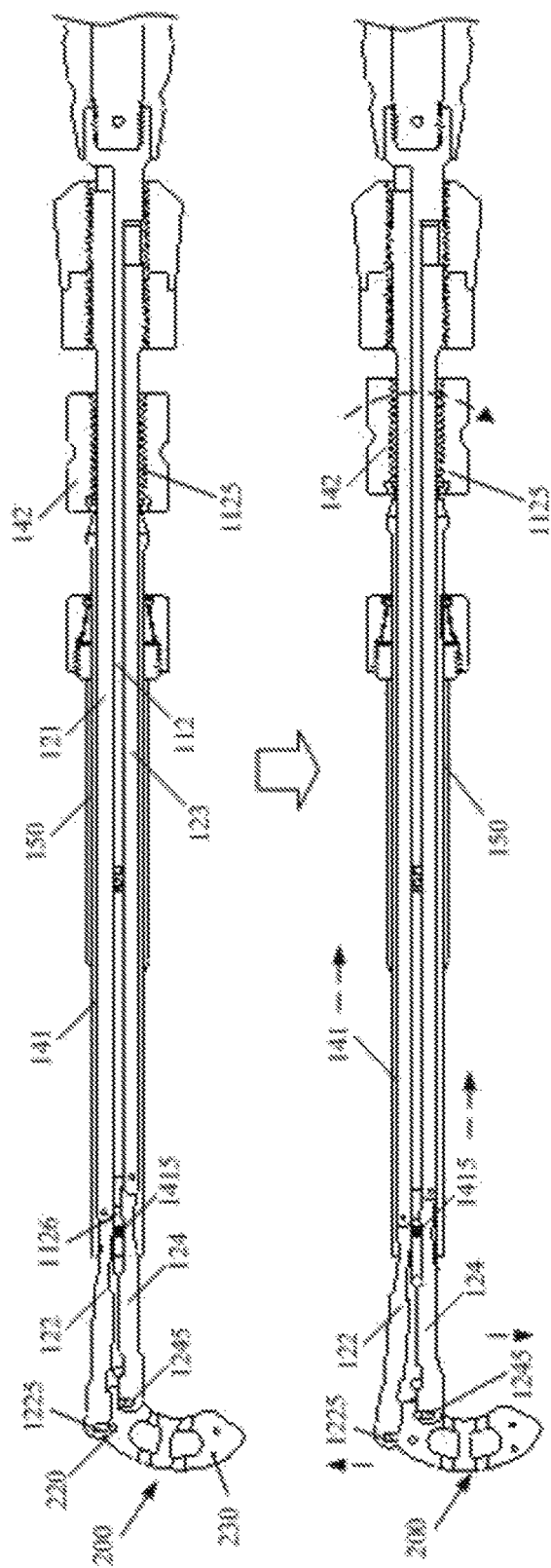
FIG. 5 is a schematic diagram for showing the relief operations of the intervertebral cage of the present invention.

Please refer to FIG. 1 and FIG. 5 together. The sleeve 141 of the second control subassembly 140 is connected to the gripping rotating shaft 142 and sheathed outside the fixed rod 112. An internal thread of the gripping rotating shaft 142 is screwed to a thread outer diameter 1125 of the fixed rod 112. When the surgeon rotates the second control subassembly 140, the sleeve 141 moves linearly toward the first end 1121 or the second end 1122 along the fixed rod 112 according to the rotation direction, so as to close or open the jaw portion 128. Furthermore, the fixed rod 112 further includes a straight limit slot 1126 near a side of the second end 1122, and the sleeve 141 further includes a stop pin 1415, and the stop pin is inserted into the straight limit slot 1126. When rotating the second control subassembly 140 to enable the sleeve 141 to move toward the first end 1121 of the fixed rod 112, the stop pin 1415 resists against, the guiding shapes of the first gripping member 122 and the second gripping member 124, such that the first fastening slot 1225 and the second fastening slot 1245 of the jaw portion 128 are able to separate from the dowel pin 220 of the gripping end 212 smoothly. As a result, technical problems, such as vibration, displacement and so on, during the releasing the intervertebral cage by using the current instrument is able to be resolved. In practice, the ends of the first gripping member 122 and the second gripping member 124 may be designed as the corresponding guiding shapes according to the actual requirements.

Please refer to FIG. 1 and FIG. 3 together. The present invention further provides an intervertebral cage 200 which includes a body 210, two dowel pins 220, and an auxiliary dowel pin 230. The body 210 has a structure comprising a plurality of penetration cavities 215 which are mutual interlaced, and upper and lower surfaces of the body 210 may be disposed with uneven surface to increase the contact area between the two spine bones and the intervertebral cage 200, such that the displacement or separation of the intervertebral cage 200 caused by external force may be avoided after the intervertebral cage 200 is implanted. In practice, the penetration holes formed by the penetration cavities 215 enable the bone cells, nerves, blood vessels and so on of the patient penetrating or adhering between the bone cells, nerves, blood vessels and so on of the patient so as to promote the efficiency of the healing. However, when a removal ratio of the volume of the body 210 by the penetration cavities 215 is too high, the entire strength of the intervertebral cage 200 may be affected and the structure thereof may even be damaged. When the removal ratio is too small, the degree of the self-healing of the patient's cells may be affected. As a result, the plurality of penetration cavities 215 remove a volume of the body 210 by 30-70%, and preferably, by 35-65%.

The body 210 may be a bent formation such as peas or a meniscus, or a bullet shape. The body 210 includes a guiding end 211 and a gripping end 212. The guiding end 211 is a streamline shape with a sharp angle, which is able to peel off or penetrate the surrounding tissues of the intervertebral disks effortlessly and effectively reduce the residual force formed between the intervertebral disks. In practice, the body 210 is shaped with a guided circumferential angle to avoid damaging surrounding tissues such as nerves, blood vessels and so on accidentally in the process of the surgery. The gripping end 212 of the body 210 is disposed with two dowel holes 2125 in parallel and the guiding end 211 is disposed with at least one auxiliary dowel hole 2115. The two dowel pins 220 and the auxiliary dowel pin 230 are penetrated in the corresponding holes arranged on the body 210. The two dowel pins 220 disposed in parallel is not only able to be gripped by the gripper subassembly 120 of the implant instrument 100, but also applied in the positioning by the C-arm in the process of the surgery. The intervertebral cage 200 of the present invention applies a relative position between the two dowel pins 220 and the auxiliary dowel pin 230 to promptly correct the direction and angle which the intervertebral cage 200 are implanted to, so as to shorten the positioning time. In practice, using various numbers and diameters of the dowel pins 220 and the auxiliary dowel pin 230 may facilitate the surgeon to see a dynamic position of the implant instrument 100 and the intervertebral cage 200 clearly in the process of the surgery, so as to enhance the positioning accuracy in the process of the surgery.

Figure 6:
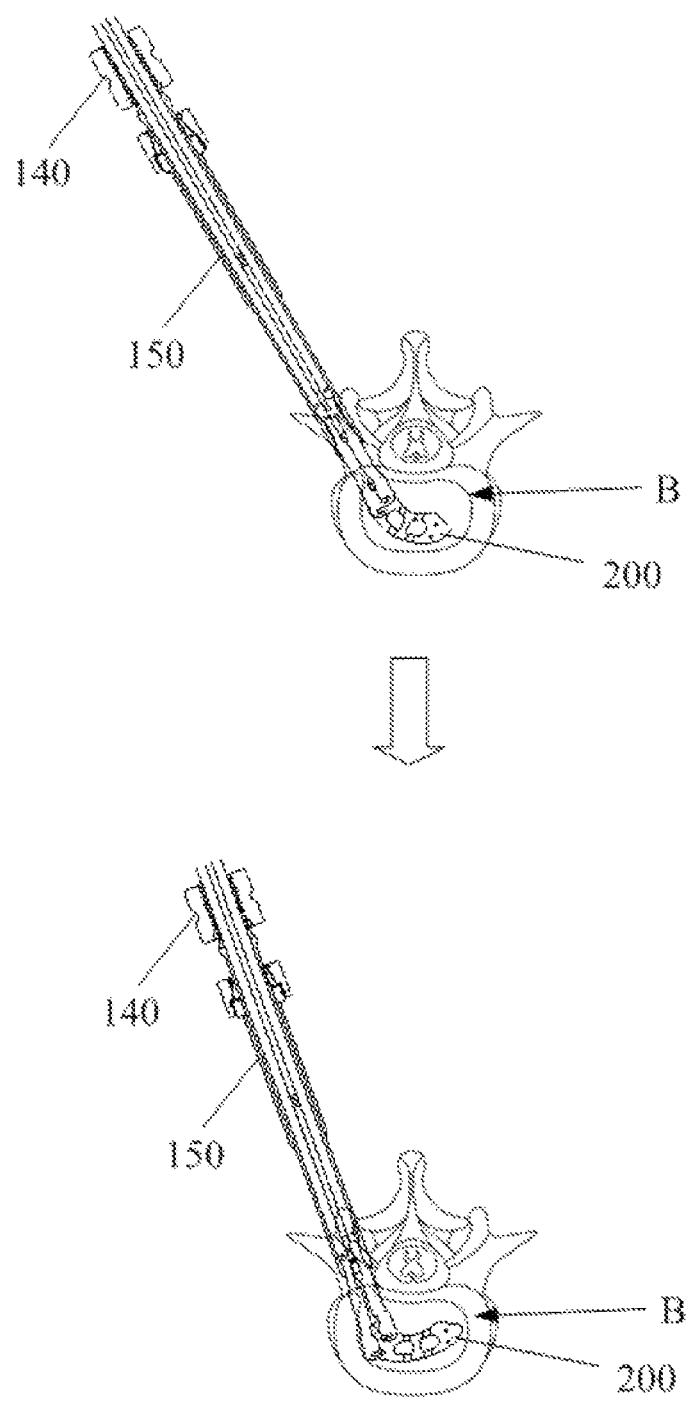
FIG. 6 is a schematic diagram for showing the Transforaminal Lumbar Interbody Fusion by means of the spinal fusion surgery instrument for implanting and the intervertebral cage thereof of the present invention.

Please refer to FIG. 4, FIG. 5, and FIG. 6 together. When the implant instrument 100 grips and implants the intervertebral cage 200 to the mounting position of the intervertebral foramen B, the surgeon implants the implant instrument 100 into the human body slowly. When the intervertebral cage 200 contacts the surface of the spine bone, the surgeon releases and moves the measuring unit 150 to the scale 0 and then re-blocks and re-fixes on the sleeve 141 to complete the step of positioning calibration. When the surgeon keeps pushing the intervertebral cage 200, the scales of the measuring unit 150 displays a depth where the implant instrument 100 and the intervertebral cage 200 insert into vertebra.

When the intervertebral cage 200 is confirmed to be located in the mounting position through the display device (not shown) and the measuring unit 150 or by the double checking of the display device and the measuring unit 150, the surgeon holds the measuring unit 150 in one hand and the other hand rotates the first control subassembly 130 to hereby change the gripping positions between the implant instrument 100 and the intervertebral cage 200 to rotate the intervertebral cage 200 for fitting the intervertebral cage 200 into an optimal mounting position. Moreover, when the intervertebral cage 200 is located in the mounting position, the surgeon operates the second control subassembly 140 to separate the intervertebral cage 200 from the implant instrument 100 smoothly.

The implant instrument of the present invention is able to adjust an angle with respect to the location of the intervertebral cage by adjusting the relative positions between each member of the gripper subassembly such that the surgeon can operate instinctively in the process of the surgery. Moreover, the implant instrument of the present invention releases the intervertebral cage 200 smoothly to reduce the positioning error. The intervertebral cage of the present invention further applies a relative position between the two dowel pins and the auxiliary dowel pin to promptly correct the direction and angle whereto the intervertebral cage is implanted, so as to shorten the positioning time.

Furthermore, when the actuating member of the existing device is an elastic member or a flexible member, the implant instrument of the present invention is able to reduce the expected factors such as elastic fatigue, delayed movement and so on by adjusting the relative movement between the stiffener members, such that the uncertainty in the operational process can be avoided.

While the means of specific embodiments in present invention has been described by reference drawings, numerous modifications and variations could be made thereto by those skilled in the art without departing from the scope and spirit of the disclosure set forth in the claims. The modifications and variations should in a range limited by the specification of the present invention.

What is claimed is:

1. An implant instrument for gripping and implanting an intervertebral cage into a location between two adjacent spine bones, the intervertebral cage comprising a gripping end and a guiding end, and the implant instrument comprising:

a body comprising a grasp rod and a fixed rod, the fixed rod having a first end and a second end, the first end being disposed at the grasp rod, the fixed rod comprising a first guiding slot and a second guiding slot which communicate with the second end, and the fixed rod having a thread outer diameter near a side of the first end;

a gripper subassembly comprising a first connecting member, a first gripping member, a second connecting member and a second gripping member, the first connecting member being connected to the first gripping member and disposed in the first guiding slot, the second connecting member being connected to the second gripping member and disposed in the second guiding slot, the first connecting member having a first thread structure and the second connecting member having a second thread structure, the first gripping member having a first fastening slot and the second gripping member having a second fastening slot, wherein the first fastening slot and the second fastening slot form a jaw portion to grip the gripping end of the intervertebral cage;

a first control subassembly comprising a first rotating shaft and a second rotating shaft, the first rotating shaft being connected to the second rotating shaft and sleeved outside the fixed rod, an internal thread of the first rotating shaft being screwed to the first thread structure and an internal thread of the second rotating shaft being screwed to the second thread structure; and a second control subassembly comprising a sleeve and a gripping rotating shaft, the sleeve being connected to the gripping rotating shaft and sheathed outside the fixed rod, an internal thread of the gripping rotating shaft being screwed to the thread outer diameter of the fixed rod;

wherein when rotating the first control subassembly, the first connecting member and the second connecting member respectively are moved to opposite directions along the first guiding slot and the second guiding slot to change a relative position between the jaw portion and the intervertebral cage so as to change an angle with respect to the location of the intervertebral cage.

2. The implant instrument of claim 1, wherein when rotating the second control subassembly, the sleeve is moved linearly along the fixed rod to open or close the jaw portion.

3. The implant instrument of claim 1, wherein the fixed rod further comprises a straight limit slot near a side of the second end, and the sleeve further comprises a stop pin, wherein the stop pin is inserted into the straight limit slot, when rotating the second control subassembly to move the sleeve toward the first end of the fixed rod, and the stop pin resists against the first gripping member and the second gripping member, such that the jaw portion opens to release the intervertebral cage.

4. The implant instrument of claim 1, wherein the first guiding slot and/or the second guiding slot further comprise a limit slot near the side of the first end of the fixed rod for limiting operation of the gripper subassembly.

5. The implant instrument of claim 1, further comprising a measuring unit measuring a depth where the implant instrument inserts into vertebra.

6. The implant instrument of claim 1, wherein the first thread structure, the second thread structure, the thread outer diameter or a combination thereof is a single thread or a multiple thread.

7. The implant instrument of claim 1, wherein the fixed rod, the first connecting member, and the second connecting member are integral or assembly-type.

8. A system comprising an intervertebral cage and an implant instrument according to claim 1, the intervertebral cage being gripped and implanted into a location between two adjacent spine bones by the implant instrument, the intervertebral cage comprising:
- a body, having a structure comprising a plurality of penetration cavities which are alternately disposed, the body having a guiding end and a gripping end, the gripping end having two dowel holes in parallel, and the gripping end being disposed with at least one auxiliary dowel hole;
- two dowel pins, inserted into the two dowel holes, respectively; and
- at least one auxiliary dowel pin inserted into the auxiliary dowel hole corresponding thereto,
- wherein the two dowel pins and the at least one auxiliary dowel pin assist in displaying and guiding a dynamic relative location of the body in a process of a surgery, and the first fastening slot and the second fastening slot are disposed in parallel to grip the two dowel pin of the intervertebral cage.

9. The system of claim 8, wherein the intervertebral cage is shaped with a guided circumferential angle to avoid damaging surrounding tissues accidentally in the process of the surgery.

10. The system of claim 8, wherein the plurality of penetration cavities remove a volume of the body by 30-70%.

\* \* \* \* \*